(12) United States Patent
Setthachayanon et al.

(10) Patent No.: US 7,229,741 B2
(45) Date of Patent: Jun. 12, 2007

(54) EXCEPTIONAL HIGH REFLECTIVE INDEX PHOTOACTIVE COMPOUND FOR OPTICAL APPLICATIONS

(75) Inventors: Songvit Setthachayanon, Longmont, CO (US); Xuan T. Phan, Raleigh, NC (US); Mark David Michaels, Colorado Springs, CO (US); Benjamin C. Ihas, Boulder, CO (US)

(73) Assignee: InPhase Technologies, Inc., Longmont, CO (US)

( * ) Notice: Subject to any disclaimer, the term of this patent is extended or adjusted under 35 U.S.C. 154(b) by 366 days.

(21) Appl. No.: 10/446,772

(22) Filed: May 29, 2003

(65) Prior Publication Data

US 2003/0224250 A1 Dec. 4, 2003

Related U.S. Application Data

(60) Provisional application No. 60/383,607, filed on May 29, 2002.

(51) Int. Cl.
*G03C 1/72* (2006.01)
*G03H 1/02* (2006.01)

(52) U.S. Cl. .......................... 430/281.1; 430/1; 430/2; 430/288.1; 359/3

(58) Field of Classification Search ...................... None
See application file for complete search history.

(56) References Cited

U.S. PATENT DOCUMENTS

| | | | |
|---|---|---|---|
| 2,522,501 A * | 9/1950 | Brooks et al. ............... 526/334 |
| 4,362,887 A * | 12/1982 | Kline .......................... 560/152 |
| 4,695,528 A | 9/1987 | Dabisch et al. |
| 5,026,860 A | 6/1991 | Buchan et al. |
| 5,332,522 A | 7/1994 | Chen et al. |
| 5,453,340 A | 9/1995 | Kawabata et al. |
| 5,558,937 A | 9/1996 | Woods et al. |
| 5,609,992 A | 3/1997 | Sorori et al. |
| 5,641,846 A | 6/1997 | Bieringer et al. |
| 5,665,494 A | 9/1997 | Kawabata et al. |
| 5,698,345 A | 12/1997 | Ohe et al. |
| 5,702,846 A * | 12/1997 | Sato et al. ...................... 430/2 |
| 5,708,064 A | 1/1998 | Coleman et al. |
| 5,807,906 A | 9/1998 | Bonvallot et al. |
| 5,891,931 A * | 4/1999 | Leboeuf et al. ................ 522/64 |
| 5,916,987 A | 6/1999 | Kobayashi et al. |
| 5,932,626 A | 8/1999 | Fong et al. |
| 5,959,775 A | 9/1999 | Joseph et al. |
| 5,969,867 A | 10/1999 | Fukushima et al. |
| 6,031,014 A | 2/2000 | Crivello |
| 6,045,953 A | 4/2000 | Ohe et al. |
| 6,048,587 A | 4/2000 | Estrin |
| 6,107,364 A | 8/2000 | Fong et al. |
| 6,124,076 A | 9/2000 | Dhar et al. |
| 6,175,037 B1 | 1/2001 | Tweedy |
| 6,194,511 B1 | 2/2001 | Momoda et al. |
| 6,221,536 B1 | 4/2001 | Dhar et al. |
| 6,310,161 B1 | 10/2001 | Weissman |
| 6,329,485 B1 * | 12/2001 | Vanderbilt ............... 526/318.1 |
| 6,423,865 B1 | 7/2002 | Strohriegl et al. |
| 6,458,908 B1 | 10/2002 | Imai et al. |
| 6,479,622 B1 | 11/2002 | Gross et al. |
| 6,482,551 B1 | 11/2002 | Dhar et al. |
| 6,743,552 B2 * | 6/2004 | Setthachayanon et al. ..... 430/1 |
| 6,780,546 B2 * | 8/2004 | Trentler et al. ................ 430/1 |
| 2005/0049376 A1 * | 3/2005 | Chisholm et al. ........... 526/256 |
| 2005/0259303 A1 * | 11/2005 | Setthachayanon et al. .... 359/15 |

FOREIGN PATENT DOCUMENTS

| | | | |
|---|---|---|---|
| EP | 945762 | * | 9/1999 |
| EP | 1026546 A1 | | 8/2000 |
| FR | 2771740 | * | 6/1999 |
| JP | 60-026012 | * | 2/1985 |
| JP | 62-056465 | * | 3/1987 |
| JP | 03-246014 | * | 11/1991 |
| JP | 07-206944 | * | 8/1995 |
| WO | 01-94430 | * | 12/2001 |

OTHER PUBLICATIONS

Beecroft et al., "High refractive index polymers for optical applications", J. Macromol. Sci.—Pure Appl. Chem., vol. A34(4) pp. 573-586 (1997).*
Patent Abstract of JP 5323850 "Hologram Recording Medium" Derwent Publication, Dec. 7, 1993.
Patent Abstract of JP 2078033 "Optical Recording Carrier" Derwent Publication, Mar. 19, 1990.
Database WPI, Section Ch, Week 199050, Derwent Publications Ltd., London, GB; AN 1990-371727, XP002254160, & JP 02 268152 A (Tokuyama Soda KK), Nov. 1, 1990.

* cited by examiner

*Primary Examiner*—Martin Angebrannt
(74) *Attorney, Agent, or Firm*—Morrison & Foerster LLP

(57) ABSTRACT

A novel liquid photoreactive asymmetric acrylate compound containing sulfur, aromatic moieties, and optionally bromine, and having high dynamic range sensitivity is disclosed. The acrylate compound is a monomer for a photo-imageable system. In one embodiment, when about 2–8% by weight of the acrylate compound is dissolved in a two-component urethane matrix system and incorporated in an optical article formed by reacting the two-component urethane matrix system, the optical article shows a sensitivity of about 4 or more and a shrinkage during the formation of the optical article of about 0.05% versus a sensitivity of 2.26 and a shrinkage of 0.13% when tribromophenyl acrylate, a commercial monomer, was used.

10 Claims, No Drawings

EXCEPTIONAL HIGH REFLECTIVE INDEX PHOTOACTIVE COMPOUND FOR OPTICAL APPLICATIONS

RELATED APPLICATION

This application claims priority from U.S. Provisional Application 60/383,607, filed May 29, 2002, which is entitled the same as this application and is incorporated herein by reference.

FIELD OF THE INVENTION

The invention relates to novel photoactive compounds, more particularly, it relates to high reflective index photoactive compounds containing sulfur and aromatic moieties for forming optical articles having excellent characteristics which can be used either alone or in combination with other compounds or polymers, whether or not photoactive, to produce exceptional high performance articles. The use of the instant photoactive compounds thus includes holographic optical data storage, optical lenses, beam steerers, and waveguides.

BACKGROUND

Developers of information storage devices and methods continue to seek increased storage capacity. As parts of this development, so-called page-wise memory systems, in particular holographic systems, have been suggested as alternatives to conventional memory devices.

In the typical holographic storage system, two coherent light beams are directed onto a storage medium. The first coherent light beam is a signal beam, which is used to encode data. The second coherent light beam is a reference light beam. The two coherent light beams intersect within the storage medium to produce an interference pattern. The storage medium records this interference pattern by changing its index of refraction to form an image of the interference pattern.

The recorded information, stored as a holographic image, can be read by illuminating the holographic image with a reference beam. When the holographic image is illuminated with a reference beam at an appropriate angle, a signal beam containing the information stored is produced. Most often the appropriate angle for illuminating the holographic image will be the same as the angle of the reference beam used for recording the holographic image. More than one holographic image may be stored in the same volume by, for example, varying the angle of the reference beam during recording.

The capabilities of holographic storage systems are limited in part by the storage media. Iron-doped lithium niobate has been used as a storage medium for research purposes for many years. However, lithium niobate is expensive, exhibits poor sensitivity (1 J/cm$^2$), has low index contrast ($\Delta$n of about 10$^{-4}$), and exhibits destructive read-out (i.e., images are destroyed upon reading). Alternatives have therefore been sought, particularly in the area of photosensitive polymer films. See, e.g., W. K. Smothers et al., "Photopolymers for Holography," SPIE OE/Laser Conference, 1212-03, Los Angeles, Calif., 1990. The material described in this article contains a photoimageable system containing a liquid monomer material (the photoactive monomer) and a photoinitiator (which promotes the polymerization of the monomer upon exposure to light), where the photoimageable system is in an organic polymer host matrix that is substantially inert to the exposure light. During writing of information into the material (by passing recording light through an array representing data), the monomer polymerizes in the exposed regions. Due to the lowering of the monomer concentration caused by the polymerization, monomer from the dark, unexposed regions of the material diffuses to the exposed regions. The polymerization and resulting concentration gradient create a refractive index change, forming the hologram representing the data. Unfortunately, deposition onto a substrate of the pre-formed matrix material containing the photoimageable system requires use of solvent, and the thickness of the material is therefore limited, e.g., to no more than about 150 µm, to allow enough evaporation of the solvent to attain a stable material and reduce void formation.

In holographic processes such as described above, which utilize three-dimensional space of a medium, the storage capacity is proportional to a medium's thickness. Thus, the need for solvent removal inhibits the storage capacity of a medium. (Holography of this type is typically referred to as volume holography because a Klein-Cook Q parameter greater than 1 is exhibited (see W. Klein and B. Cook, "Unified approach to ultrasonic light diffraction," *IEEE Transaction on Sonics and Ultrasonics*, SU-14, 1967, at 123–134). In volume holography, the media thickness is generally greater than the fringe spacing,)

U.S. Pat. No. 6,013,454 and application Ser. No. 08/698, 142, the disclosures of which are hereby incorporated by reference, also relates to a photoimageable system in an organic polymer matrix. In particular, the application discloses a recording medium formed by polymerizing matrix material in situ from a fluid mixture of organic oligomer matrix precursor and a photoimageable system. A similar type of system, but which does not incorporate oligomers, is discussed in D. J. Lougnot et al., *Pure and Appl. Optics*, 2, 383 (1993). Because little or no solvent is typically required for deposition of these matrix materials, greater thicknesses are possible, e.g., 200 µm and above. However, while useful results are obtained by such processes, the possibility exists for reaction between the precursors to the matrix polymer and the photoactive monomer. Such reaction would reduce the refractive index contrast between the matrix and the polymerized photoactive monomer, thereby affecting to an extent the strength of the stored hologram.

Thus, while progress has been made in fabricating photorecording media suitable for use in holographic storage systems, further progress is desirable. In particular, the urgent need exists for high reflective index photoactive compounds that can provide higher reflective index contrast between the matrix and the polymerized photoactive compounds with independent reaction from the matrix system. This type of compounds is not available commercially; thus, necessitate the creation of the instant products.

SUMMARY OF THE INVENTION

This invention describes novel photoactive compounds which provide exceptionally high M/#, high sensitivity, and low shrinkage when incorporated in an independent polymeric matrix holographic data storage media system. The instant photoactive compounds can be represented by the following chemical structure:

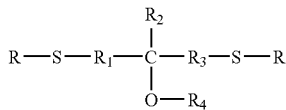

where R can be phenyl, mono or multi-substituted phenyls, bromophenyl, or naphthalene group; $R_1$ and $R_3$ can be methylene, ethylene, propylene, or butylene group; $R_2$ can be H, or alkyl group, and $R_3$ can be $COCH=CH_2$, $COCCH_3=CH_2$, or $CH=CH_2$. Synthesis, properties, and applications of the above compounds will be illustrated herein.

The M/# is defined to be the dynamic range of the recording material. The M/# is measured by multiplexing a series of holograms with exposure times set to consume all of the photoactive materials in the media. The M/# is then the sum of the square roots of the diffraction efficiencies of all of the multiplexed holograms. The M/# depends on the thickness of the media.

The sensitivity is measured by the cumulative exposure time required to reach 80% of the total M/# of the recording medium. The higher the sensitivity of the material, the shorter the cumulative exposure time required to reach 80% of the total M/#.

The shrinkage (occurring primarily in the thickness of the medium) is determined by measuring the Bragg detuning (the shift in the readout angle) of the angle multiplexed holograms. The quantitative relationship between the physical shrinkage of the material and the Bragg detuning is described in detail in the above reference, i.e., Applied Physics Letters, Volume 73, Number 10, p. 1337–1339, 7 Sep. 1998.

The inhibition time is defined as the time it takes for the holograms to form from the time the media is exposed to a light source.

DETAILED DESCRIPTION

The optical article, e.g., holographic data recording medium, of the invention is formed by steps including mixing a matrix precursor and a photoactive monomer of a photoimageable system, and curing the photoimageable system to form the matrix in situ. The matrix precursor and photoactive monomer are selected such that the following conditions are preferentially met by such the photoimageable system. (1) The photoimageable system is a "two-chemistry system" such that the reaction by which the matrix precursor is polymerized during the cure is independent from the reaction by which the photoactive monomer will be polymerized during writing of a pattern, e.g., data. (2) The matrix polymer and the polymer resulting from polymerization of the photoactive monomer (the photopolymer) are compatible with each other. As discussed previously, the matrix is considered to be formed when the photorecording material, i.e., the matrix material plus the photoactive monomer, photoinitiator, and/or other additives, exhibits an elastic modulus of at least about $10^5$ Pa, generally about $10^5$ Pa to about $10^9$ Pa, advantageously about $10^6$ Pa to about $10^8$ Pa.

The compatibility of the matrix polymer and photopolymer tends to prevent large-scale (>100 nm) phase separation of the components, such large-scale phase separation typically leading to undesirable haziness or opacity. Utilization of a photoactive monomer and a matrix precursor that polymerize by independent reactions provides a cured matrix substantially free of cross-reaction, i.e., the photoactive monomer remains substantially inert during the matrix cure. In addition, due to the independent reactions, there is no inhibition of subsequent polymerization of the photoactive monomer. At least one photoactive monomer contains one or more moieties, excluding the monomer functional groups, that are substantially absent from the polymer matrix, i.e., it is possible to find a moiety in the photoactive monomer such that no more than 20% of all such moieties in the photorecording material are present, i.e., covalently bonded, in the matrix. The resulting optical article is capable of exhibiting desirable refractive index contrast due to the independence of the matrix from the photoactive monomer.

As discussed above, formation of a hologram, waveguide, or other optical article relies on a refractive index contrast (Δn) between exposed and unexposed regions of a medium, this contrast at least partly due to monomer diffusion to exposed regions. High index contrast is desired because it provides improved signal strength when reading a hologram, and provides efficient confinement of an optical wave in a waveguide. One way to provide high index contrast in the invention is to use a photoactive monomer having moieties (referred to as index-contrasting moieties) that are substantially absent from the matrix, and that exhibit a refractive index substantially different from the index exhibited by the bulk of the matrix. For example, high contrast would be obtained by using a matrix that contains primarily aliphatic or saturated alicyclic moieties with a low concentration of heavy atoms and conjugated double bonds (providing low index) and a photoactive monomer made up primarily of aromatic or similar high-index moieties.

Preferred photoactive monomers can be represented by the following chemical structure.

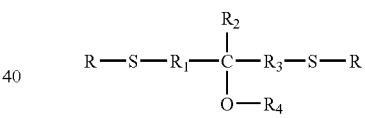

where R can be phenyl, mono or multi-substituted phenyls, bromophenyl, or naphthalene group; $R_1$ and $R_3$ can be methylene, ethylene, propylene, or butylene group; $R_2$ can be H, or alkyl group; and $R_3$ can be $COCH=CH_2$, $COCCH_3=CH_2$, or $CH=CH_2$.

The matrix is a solid polymer formed in situ from a matrix precursor by a curing step (curing indicating a step of inducing reaction of the precursor to form the polymeric matrix). It is possible for the precursor to be one or more monomers, one or more oligomers, or a mixture of monomer and oligomer. In addition, it is possible for the precursor to be greater than one type of precursor functional groups, either on a single precursor molecule or in a group of precursor molecules. (Precursor functional groups are the group or groups on a precursor molecule that are the reaction sites for polymerization during matrix cure.) To promote mixing with the photoactive monomer, the precursor is advantageously liquid at some temperature between about −50° C. and about 80° C. Advantageously, the matrix polymerization is capable of being performed at room temperature. Also advantageously, the polymerization is capable of being performed in a time period less than 5 minutes. The glass transition temperature ($T_g$) of the photorecording material is advantageously low enough to permit sufficient diffusion and chemical reaction of the photoactive monomer during a holographic recording process. Generally, the $T_g$ is not more than 50° C. above the temperature at which holographic recording is performed, which, for typical holographic recording, means a $T_g$ between about 80° C. and about –130° C. (as measured by conventional methods).

Examples of polymerization reactions contemplated for forming matrix polymers in the invention include isocyanate-hydroxyl step polymerization (urethane formation), isocyanatae-amine step polymerization (urea formation), cationic epoxy polymerization, cationic vinyl ether polymerization, cationic alkenyl ether polymerization, cationic allene ether polymerization, cationic ketene acetal polymerization, epoxy-amine step polymerization, epoxy-mercaptan step polymerization, unsaturated ester-amine step polymerization (via Michael addition), unsaturated ester-mercaptan step polymerization (via Michael addition), and vinyl-silicon hydride step polymerization (hydrosilylation).

Several such reactions are enabled or accelerated by suitable catalysts. For example, cationic epoxy polymerization takes place rapidly at room temperature by use of $BF_3$-based catalysts, other cationic polymerizations proceed in the presence of protons, epoxy-mercaptan reactions and Michael additions are accelerated by bases such as amines, hydrosilylation proceeds rapidly in the presence of transition metal catalysts such as platinum, and urethane and urea formation proceed rapidly when tin catalysts are employed. It is also possible to use photogenerated catalysts for matrix formation, provided that steps are taken to prevent polymerization of the photoactive monomer during the photogeneration.

The photoactive monomer is any monomer or monomers capable of undergoing photoinitiated polymerization, and which, in combination with a matrix material, meets the polymerization reaction and compatibility requirements of the invention. Suitable photoactive monomers include those which polymerize by a free-radical reaction, e.g., molecules containing ethylenic unsaturation such as acrylates, methacrylates, acrylamides, methacrylamides, styrene, substituted styrenes, vinyl naphthalene, substituted vinyl naphthalenes, and other vinyl derivatives. Free-radical copolymerizable pair systems such as vinyl ether mixed with maleate and thiol mixed with olefin are also suitable. It is also possible to use cationically polymerizable systems such as vinyl ethers, alkenyl ethers, allene ethers, ketene acetals, and epoxies. It is also possible for a single photoactive monomer molecule to contain more than one monomer functional group. These monomers could used as by themselves or in combination in a mixture.

As mentioned previously, relatively high index contrast is desired in the article of the invention, whether for improved readout in a recording media or efficient light confinement in a waveguide. In addition, it is advantageous to induce this relatively large index change with a small number of monomer functional groups, because polymerization of the monomer generally induces shrinkage in a material.

Such shrinkage has a detrimental effect on the retrieval of data from stored holograms, and also degrades the performance of waveguide devices such as by increased transmission losses or other performance deviations. Lowering the number of monomer functional groups that must be polymerized to attain the necessary index contrast is therefore desirable. This lowering is possible by increasing the ratio of the molecular volume of the monomers to the number of monomer functional groups on the monomers. This increase is attainable by incorporating into a monomer larger index-contrasting moieties and/or a larger number of index-contrasting moieties. For example, if the matrix is composed primarily of aliphatic or other low index moieties and the monomer is a higher index species where the higher index is imparted by a benzene ring, the molecular volume could be increased relative to the number of monomer functional groups by incorporating a naphthalene ring instead of a benzene ring (the naphthalene having a larger volume), or by incorporating one or more additional benzene rings, without increasing the number of monomer functional groups. In this manner, polymerization of a given volume fraction of the monomers with the larger molecular volume/monomer functional group ratio would require polymerization of less monomer functional groups, thereby inducing less shrinkage. But the requisite volume fraction of monomer would still diffuse from the unexposed region to the exposed region, providing the desired refractive index.

The molecular volume of the monomer, however, should not be so large as to slow diffusion below an acceptable rate. Diffusion rates are controlled by factors including size of diffusing species, viscosity of the medium, and intermolecular interactions. Larger species tend to diffuse more slowly, but it would be possible in some situations to lower the viscosity or make adjustments to the other molecules present in order to raise diffusion to an acceptable level. Also, in accord with the discussion herein, it is important to ensure that larger molecules maintain compatibility with the matrix.

Numerous architectures are possible for monomers containing multiple index-contrasting moieties. For example, it is possible for the moieties to be in the main chain of a linear oligomer, or to be substituents along an oligomer chain. Alternatively, it is possible for the index-contrasting moieties to be the subunits of a branched or dendritic low molecular weight polymer. The preferred photoactive monomers are disclosed above.

Typically, 0.1 to 20 wt. % photoactive monomer, based on the weight of the photoimageable system, provides desirable results. The preferred acrylate monomers are monofunctional. These include 2,4,6-tribromophenylacrylate; 2,4-bis (2-naphthylthio)-2-butylacrylate; pentabromoacrylate; isobornylacrylate; phenylthioethyl acrylate; tetrahydrofurfurylacrylate; 1-vinyl-2-pyrrolidinone; 2-phenoxyethylacrylate; and the like.

In addition to the photoactive monomer, the optical article typically contains a photoinitiator (the photoinitiator and photoactive monomer being part of the overall photoimageable system). The photoinitiator, upon exposure to relatively low levels of the recording light, chemically initiates the polymerization of the monomer, avoiding the need for direct light-induced polymerizatioin of the monomer. The photoinitiator generally should offer a source of species that initiate polymerization of the particular photoactive monomer. Typically, 0.1 to 20 wt. % photoinitiator, based on the weight of the photoimageable system, provides desirable results.

A variety of photoinitiators known to those skilled in the art and available commercially are suitable for use in the invention. It is advantageous to use a photoinitiator that is sensitive to light in the visible part of the spectrum, particularly at wavelengths available from conventional laser sources, e.g., the blue and green lines of Ar+ (458, 488, 514 nm) and He—Cd lasers (442 nm), the green line of frequency doubled YAG lasers (532 nm), and the red lines of He—Ne (633 nm) and Kr+lasers (647 and 676 nm). One advantageous free radical photoinitiator is bis(η-5-2,4-cyclopentadien-1-yl)bis[2,6-difluoro-3-(1H-pyrrol-1-yl)phenyl]titanium, available commercially from Ciba as Irgacure-784. Another visible free-radical photoinitiator (which requires a co-initiator) is 5,7,diiodo-3-butoxy-6-fluorone, commercially available from Spectra Group Limited as H—Nu 470. Free-radical photoinitiators of dye-hydrogen donor systems are also possible. Examples of suitable dyes include eosin, rose bengal, erythrosine, and methylene blue, and suitable hydrogen donors include tertiary amines such as n-methyl diethanol amine. In the case of cationically polymerizable monomers, a cationic photoinitiator is used, such as a sulfonium salt or an iodonium salt. These cationic photoinitiator salts absorb predominantly in the UV portion of the spectrum, and are therefore typically sensitized with a dye to allow use of the visible portion of the spectrum. An example of an alternative visible cationic photoinitiator is ($\eta_5$-2,4-cyclopentadien-1-yl) ($\eta_6$-isopropylbenzene)-iron (II) hexafluorophosphate, available commercial from Ciba as Irgacure 261. It is also conceivable to use other additives in the photoimageable system, e.g., inert diffusing agents having relatively high or low refractive indices.

Preferably, the photoinitiators are selected according to their sensitivity to the light sources. For example, Irgacure 369, Irgacure 819, and Irgacure 907 are suitable for commercial blue laser systems. Irgacure-784 is suitable for green laser systems, and CB-650 is suitable for red laser systems. Irgacure products are available from Ciba; CB-650 is available from the Spectra Group.

Advantageously, for holographic recording, the matrix is a polymer formed by isocyanate-hydroxyl step polymerization, more advantageously a polymer formed by isocyanate-hydroxyl step polymerization having a polyether backbone. The polyether backbone offers desirable compatibility with several useful photoactive monomers, particularly vinyl aromatic compounds. Specifically, photoactive monomers selected from styrene, bromostyrene, divinyl benzene, and 4-methylthio-1-vinylnaphthalene (MTVN) have been found to be useful with matrix polymers formed by isocyanate-hydroxyl step polymerization and having a polyether backbone. A monomer that has more than one index-contrasting moiety and that is also useful with these polyether matrix polymers is 1-(3-(naphth-1-ylthio)propylthio)-4-vinylnaphthalene. Other more preferred monomers include 2,4-bis(2-naphthylthio)-2-butylacrylate, and tribromophenyl acrylate.

To be independent, the polymerization reactions for the matrix precursor and the photoactive monomer are selected such that: (a) the reactions proceed by different types of reaction intermediates, (b) neither the intermediate nor the conditions by which the matrix is polymerized will induce substantial polymerization of the photoactive monomer functional groups, and (c) neither the intermediate nor the conditions by which the matrix is polymerized will induce a non-polymerization reaction of the monomer functional groups that causes cross-reaction (between the monomer functional groups and the matrix polymer) or inhibits later polymerization of the monomer functional groups. According to item (a), if a matrix is polymerized by use of an ionic intermediate, it would be suitable to polymerize the photoactive monomer by use of a free radical reaction. In accordance with item (b), however, the ionic intermediate should not induce substantial polymerization of the photoactive monomer functional groups. Also in accordance with item (b), for example, one must be aware that a photoinitiated free radical matrix polymerization will typically induce a photoinitiated cationic polymerization of a photoactive monomer functional group. Thus, two otherwise independent reactions are not independent for purposes of the invention if both are driven by a single reaction condition. In accordance with item (c), for example, base-catalyzed matrix polymerization should not be performed when the photoactive monomer functional group undergoes a non-polymerization reaction in response to the base, even if polymerization of the monomer functional group is performed by an independent reaction. A specific example is that a base-catalyzed epoxy-mercaptan polymerization should not be used with an acrylate monomer because, although the acrylate is polymerized by a free radical reaction, the acrylate will react with the mercaptans under base catalysis, resulting in a cross-reaction.

Table 1 below illustrates some examples of matrix/photoactive monomer combinations where the matrix polymerization reaction and photoactive monomer polymerization are capable of being independent, and examples where the polymerizations interfere with each other. (Photoactive monomers are horizontal, and matrix polymers are vertical. "X" indicates cross-reaction or monomer polymerization during matrix polymerization. "O" indicates independent reactions. "I" indicates that the photoactive monomer polymerization is inhibited by the reagents or reaction that form the polymeric matrix, e.g., the photoactive monomer functional group is converted to a non-polymerizing group, or chemical species are present after the matrix cure that substantially slow the rate or yield of polymerization of the monomer functional groups.)

TABLE 1

|  | (Meth) acrylates | Styrene Derivatives | Vinyl Ethers | Epoxies |
|---|---|---|---|---|
| Cationic Epoxy | O | O | X | X |
| Cationic Vinyl Ethers | O | O | X | X |
| Epoxy (amine) | X | O | I | X |
| Epoxy (mercaptan) | X | O | I | X |
| Unsaturated ester (amine) | X | O | I | X |
| Unsaturated ester (mercaptan) | X | O | I | X |
| Hydrosilylation | X | X | X | O |
| Urethane formation | O | O | O | X |

For purposes of the invention, polymers are considered to be compatible if a blend of the polymers is characterized, in 90° light scattering, by a Rayleigh ratio ($R_{90°}$) less than $7 \times 10^{-3}$ cm$^{-1}$. The Rayleigh ratio, $R_\theta$, is a conventionally known property, and is defined as the energy scattered by a unit volume in the direction $\theta$, per steradian, when a medium is illuminated with a unit intensity of unpolarized light, as discussed in M. Kerker, *The Scattering of Light and Other Electromagnetic Radiation*, Academic Press, San Diego, 1969. The light source used for the measurement is generally a laser having a wavelength in the visible part of the spectrum. Normally, the wavelength intended for use in writing holograms is used. The scattering measurements are made upon a photorecording material that has been flood exposed. The scattered light is collected at an angle of 90° from the incident light, typically by a photodetector. It is possible to place a narrowband filter, centered at the laser wavelength, in front of such a photodetector to block fluorescent light, although such a step is not required. The Rayleigh ratio is typically obtained by comparison to the energy scatter of a reference material having a known Rayleigh ratio.

Polymer blends, which are considered to be miscible, e.g., according to conventional tests such as exhibition of a single glass transition temperature, will typically be compatible as well, i.e., miscibility is a subset of compatibility. Standard miscibility guidelines and tables are therefore useful in selecting a compatible blend. However, it is possible for polymer blends that are immiscible to be compatible according to the light scattering test above.

A polymer blend is generally considered to be miscible if the blend exhibits a single glass transition temperature, $T_g$, as measured by conventional methods. An immiscible blend will typically exhibit two glass transition temperatures corresponding to the $T_g$ values of the individual polymers. $T_g$ testing is most commonly performed by differential scanning calorimetry (DSC), which shows the $T_g$ as a step change in the heat flow (typically the ordinate). The reported $T_g$ is typically the temperature at which the ordinate reaches the mid-point between extrapolated baselines before and after the transition. It is also possible to use Dynamic Mechanical Analysis (DMA) to measure $T_g$. DMA measures the storage modulus of a material, which drops several orders of magnitude in the glass transition region. It is possible in certain cases for the polymers of a blend to have individual $T_g$ values that are close to each other. In such cases, conventional methods for resolving such overlapping $T_g$ should be used, such as discussed in Brinke et al., "The thermal characterization of multi-component systems by enthalpy relaxation," *Thermochimica Acta.*, 238 (1994), at 75.

Matrix polymer and photopolymer that exhibit miscibility are capable of being selected in several ways. For example, several published compilations of miscible polymers are available, such as O. Olabisi et al, *Polymer-Polymer Miscibility*, Academic Press, New York, 1979; L. M. Robeson, *MMI, Press Symp. Ser.*, 2, 177, 1982; L. A. Utracki, *Polymer Alloys and Blends: Thermodynamics and Rheology*, Hanser Publishers, Munich, 1989; and S. Krause in *Polymer Handbook*, J. Brandrup and E. H. Immergut, Eds., 3rd Ed., Wiley Interscience, New York, 1989, pp. VI 347–370, the disclosures of which are hereby incorporated by reference. Even if a particular polymer of interest is not found in such references, the approach specified allows determination of a compatible photorecording material by employing a control sample.

Determination of miscible or compatible blends is further aided by intermolecular interaction considerations that typically drive miscibility. For example, it is well known that polystyrene and poly(methylvinylether) are miscible because of an attractive interaction between the methyl ether group and the phenyl ring. It is therefore possible to promote miscibility, or at least compatibility, of two polymers by using a methyl ether group in one polymer and a phenyl group in the other polymer. It has also been demonstrated that immiscible polymers are capable of being made miscible by the incorporation of appropriate functional groups that can provide ionic interactions. (See Z. L. Zhou and A. Eisenberg, *J. Polym. Sci., Polym. Phys. Ed.*, 21 (4), 595, 1983; R. Murali and A. Eisenberg, *J. Polym. Sci., Part B: Polym. Phys.*, 26 (7), 1385, 1988; and A Natansohn et al., *Makromol. Chem., Macromol. Sym*, 16, 175, 1988). For example polyisoprene and polystyrene are immiscible. However, when polyisoprene is partially sulfonated (5%), and 4-vinyl pyridine is copolymerized with the polystyrene, the blend of these two functionalized polymers is miscible. It is contemplated that the ionic interaction between the sulfonated groups and the pyridine group (proton transfer) is the driving force that makes this blend miscible. Similarly, polystyrene and poly(ethyl acrylate), which are normally immiscible, have been made miscible by lightly sulfonating the polystyrene. (See R. E. Taylor-Smith and R. A. Register, *Macromolecules*, 26, 2802, 1993.) Charge-transfer has also been used to make miscible polymers that are otherwise immiscible. For example it has been demonstrated that, although poly(methyl acrylate) and poly(methyl methacrylate) are immiscible, blends in which the former is copolymerized with (N-ethylcarbazol-3-yl)methyl acrylate (electron donor) and the latter is copolymerized with 2-[(3,5-dinitrobenzoyl)oxy]ethyl methacrylate (electron acceptor) are miscible, provided the right amounts of donor and acceptor are used. (See M. C. Piton and A. Natansohn, *Macromolecules*, 28, 15, 1995.) Poly(methyl methacrylate) and polystyrene are also capable of being made miscible using the corresponding donor-acceptor co-monomers (See M. C. Piton and A. Natansohn, *Macromolecules*, 28, 1605, 1995).

A variety of test methods exist for evaluating the miscibility or compatibility of polymers, as reflected in the recent overview published in A. Hale and H. Bair, Ch. 4—"Polymer Blends and Block Copolymers," *Thermal Characterization of Polymeric Materials*, 2nd Ed., Academic Press, 1997. For example, in the realm of optical methods, opacity typically indicates a two-phase material, whereas clarity generally indicates a compatible system. Other methods for evaluating miscibility include neutron scattering, infrared spectroscopy (IR), nuclear magnetic resonance (NMR), x-ray scattering and diffraction, fluorescence, Brillouin scattering, melt titration, calorimetry, and chemilluminescence. See, for example, L. Robeson, supra; S. Krause, *Chemtracts—Macromol. Chem.*, 2, 367, 1991a; D. Vessely in *Polymer Blends and Alloys*, M. J. Folkes and P. S. Hope, Eds., Blackie Academic and Professional, Glasgow, pp. 103–125; M. M. Coleman et al. *Specific Interactions and the Miscibility of Polymer Blends*, Technomic Publishing, Lancaster, Pa., 1991; A. Garton, *Infrared Spectroscopy of Polymer Blends, Composites and Surfaces*, Hanser, N.Y., 1992; L. W. Kelts et al., *Macromolecules*, 26, 2941, 1993; and J. L. White and P. A. Mirau, *Macromolecules*, 26, 3049, 1993; J. L. White and P. A. Mirau, *Macromolecules*, 27, 1648, 1994; and C.A. Cruz et al., *Macromolecules*, 12, 726, 1979; and C. J. Landry et al., *Macromolecules*, 26, 35, 1993.

Compatibility has also been promoted in otherwise incompatible polymers by incorporating reactive groups into the polymer matrix, where such groups are capable of reacting with the photoactive monomer during the holographic recording step. Some of the photoactive monomer will thereby be grafted onto the matrix during recording. If there are enough of these grafts, it is possible to prevent or reduce phase separation during recording. However, if the refractive index of the grafted moiety and of the monomer is relatively similar, too many grafts, e.g., more than 30% of monomers grafted to the matrix, will tend to undesirably reduce refractive index contrast.

A holographic recording medium of the invention is formed by adequately supporting the photorecording material, such that holographic writing and reading is possible. Typically, fabrication of the medium involves depositing the matrix precursor/photoimageable system mixture between two plates using, for example, a gasket to contain the mixture. The plates are typically glass, but it is also possible to use other materials transparent to the radiation used to write data, e.g., a plastic such as polycaronate or poly (methyl methacrylate). It is possible to use spacers between the plates to maintain a desired thickness for the recording medium. During the matrix cure, it is possible for shrinkage in the material to create stress in the plates, such stress altering the parallelism and/or spacing of the plates and thereby detrimentally affecting the medium's optical properties. To reduce such effects, it is useful to place the plates in an apparatus containing mounts, e.g., vacuum chucks, capable of being adjusted in response to changes in parallelism and/or spacing. In such an apparatus, it is possible to monitor the parallelism in real-time by use of a conventional interferometric method, and make any necessary adjustments during the cure. Such a method is discussed, for example, in U.S. patent application Ser. No. 08/867,563, the disclosure of which is hereby incorporated by reference. The photorecording material of the invention is also capable of being supported in other ways. For instance, it is conceivable to dispose the matrix precursor/photoimageable system mixture into the pores of a substrate, e.g., a nanoporous glass material such as Vycor, prior to matrix cure. More conventional polymer processing is also invisioned, e.g., closed mold formation or sheet extrusion. A stratified medium is also contemplated, i.e., a medium containing multiple substrates, e.g., glass, with layers of photorecording material disposed between the substrates.

The medium of the invention is then capable of being used in a holographic system such as discussed previously. The amount of information capable of being stored in a holographic medium is proportional to the product of: the refractive index contrast, $\Delta n$, of the photorecording material, and the thickness, d, of the photorecording material. (The refractive index contract, $\Delta n$, is conventionally known, and is defined as the amplitude of the sinusoidal variations in the refractive index of a material in which a plane-wave, volume hologram has been written. The refractive index varies as: $n(x)=n_0+\Delta n \cos(K_x)$, where $n(x)$ is the spatially varying refractive index, x is the position vector, K is the grating wavevector, and $n_0$ is the baseline refractive index of the medium. See, e.g., P. Hariharan, *Optical Holography: Principles, Techniques, and Applications,* Cambridge University Press, Cambridge, 1991, at 44.) The $\Delta n$ of a material typically calculated from the diffraction efficiency or efficiencies of a single volume hologram or a multiplexed set of volume holograms recorded in a medium. The $\Delta n$ is associated with a medium before writing, but is observed by measurement performed after recording. Advantageously, the photorecording material of the invention exhibits a $\Delta$ of $3\times10^{-3}$ or higher.

Examples of other optical articles include beam filters, beam steerers or deflactors, and optical couplers. (See, e.g., L. Solymar and D. Cooke, *Volume Holography and Volume Gratings,* Academic Press, 315–327 (1981), the disclosure of which is hereby incorporated by reference.) A beam filter separates part of an incident laser beam that is traveling along a particular angle from the rest of the beam. Specifically, the Bragg selectivity of a thick transmission hologram is able to selectively diffract light along a particular angle of incidence, while light along other angle travels undeflected through the hologram. (See, e.g., J. E. Ludman et al., "Very thick holographic nonspatial filtering of laser beams," *Optical Engineering,* Vol. 36, No. 6, 1700 (1997), the disclosure of which is hereby incorporated by reference.) A beam steerer is a hologram that deflects light incident at the Bragg angle. An optical coupler is typically a combination of beam deflectors that steer light from a source to a target. These articles, typically referred to as holographic optical elements, are fabricated by imaging a particular optical interference pattern within a recording medium, as discussed previously with respect to data storage. Medium for these holographic optical elements are capable of being formed by the techniques discussed herein for recording media or waveguides.

As mentioned previously, the material principles discussed herein are applicable not only to hologram formation, but also to formation of optical transmission devices such as waveguides. Polymeric optical waveguides are discussed for example in B. L. Booth, "Optical Interconnection Polymers," in *Polymers for Lightwave and Integrated Optics, Technology and Applications,* L. A. Hornak, ed., Marcel Dekker, Inc. (1992); U.S. Pat. Nos. 5,292,620; and 5,219,710, the disclosures of which are hereby incorporated by reference. Essentially, the recording material of the invention is irradiated in a desired waveguide pattern to provide refractive index contrast between the waveguide pattern and the surrounding (cladding) material. It is possible for exposure to be performed, for example, by a focused laser light or by use of a mask with a non-focused light source. Generally, a single layer is exposed in this manner to provide the waveguide pattern, and additional layers are added to complete the cladding, thereby completing the waveguide. The process is discussed for example at pages 235–36 of Booth, supra, and Cols. 5 and 6 of U.S. Pat. No. 5,292,620. A benefit of the invention is that by using conventional molding techniques, it is possible to mold the matrix/photoimageable system mixture into a variety of shapes prior to matrix cure. For example, the matrix/photoimageable system mixture can be molded into ridge waveguides, wherein refractive index patterns are then written into the molded structures. It is thereby possible to easily form structures such as Bragg gratings. This feature of the invention increases the breadth of applications in which such polymeric waveguides would be useful.

In one embodiment, the present invention comprises the following ingredients:

| | |
|---|---|
| NCO-terminated prepolymers | 20–50 Wt % |
| Photoactive Monomers | 1–15 Wt % |
| Photoinitiators | 0.2–3 Wt % |
| Polyols | 40–75 Wt % |
| Catalysts | 0.1–3 Wt % |
| Thermal Stabilizers and Oxidizers | 0.001–0.5 Wt % |

The NCO-terminated prepolymers are selected from the by-products of diols and diisocyanates that have wt % contents of NCO in the range of 10 to 25. The NCO contents were determined based on the prepolymer, unreacted diisocyanate and optionally added neat polyisocyanates to achieve the high performance characteristics. Preferred NCO-terminated prepolymers are the reaction products of polyether polyols with polyisocyanates. Some commercially available products can be used; for example, from Bayer Corporation: Baytec WE-series, ME-series, MP-series, and MS-series; from Air Products and Chemicals: the Airthane series. Aliphatic polyisocynates based prepolymers are preferred. However, when the NCO-terminated prepolymer is based on aliphatic diisocyanates, 5 to 100% of its wt % contents of NCO have to be derived from aromatic diisocyanates or aliphatic polyisocyanates. Preferred aromatic diisocyanates are, but no limit to, diphenylmethane diisocyanate (MDI) and toluene diisocyanate (TDI). More preferred are aliphatic polyisocyanates such as Hexamethylene diisocyanate (HDI) and its biuret, isocyanurate, uretidione derivatives; methylene di(cyclohexylisocyanate); trimethylhexamethylenediisocyanates; and isophoronediisocyanate.

Preferred photoactive monomers can be represented by the following chemical structure:

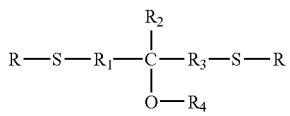

where R can be phenyl, mono or multi-substituted phenyls, bromophenyl, or naphthalene group; $R_1$ and $R_3$ can be methylene, ethylene, propylene, or butylene group; $R_2$ can be H, or alkyl group; $R_3$ can be $COCH=CH_2$, $COCCH_3=CH_2$, or $CH=CH2$.

Two acrylate compounds as examples to the above chemical structure are 2,4-bis(2-naphthylthio)-2-butylacrylate and 1,4-bis(4Bromophenylthio)-2-butylacrylate. The preferred acrylate monomers are monofunctional. These include 2,4, 6-tribromophenylacrylate; pentabromoacrylate; isobornylacrylate; phenylthioethyl acrylate tetrahydrofurfurylacrylate; 2,4-bis(2-naphthylthio)-2-butylacrylate; 1-vinyl-2-pyrrolidinone; 1,4-bis(4-bromobenzenethio)-2-butanol; 2-phenoxyethylacrylate; and the like. The most preferred acrylate monomer is 2,4-bis(2-naphthylthio)-2-butylacrylate and 1,4-bis(4-bromobenzenethio)-2-butanol.

Preferably, the photoinitiators are selected according to their sensitivity to the light sources. For example, Irgacure 369, Irgacure 819, and Irgacure 907 are suitable for commercial blue laser systems. Irgacure 784 is suitable for green laser systems, and CB-650 is suitable for red laser systems. Irgacure products are available from Ciba, CB-650 is available from the Spectra Group.

Polyols are selected from diols and triols of polytetramethylene glycol, polycaprolactone, polypropylene oxide. Preferred polyols are polypropylene oxide triols with molecular weight ranging from 450 to 6,000. Preferably the polyols are free of moisture contents. High temperature vacuum distillation treatments or additives such as moisture scavengers may be used to assure no water residue remains in the polyols before use.

Tin catalysts could be used. These are dimethyltin carboxylate, dimethyltindilaurate, dibutyltindilaurate, stannous octoate, and others.

Additives include thermal stabilizers such as butyrated hydroxytoluene (BHT), tri(N-nitroso-N-phenylhydroxylamine)aluminum salt (NPAL), Phenothiazine, hydroquinone, and methylether of hydroquinone; reducers such as peroxides, phosphites, and hydroxyamines; and deformers or deaerators to eliminate entrapped air bubbles.

It has been found that an aluminum salt compound, used by itself or in combination with other thermal stabilizers, provide the desired stability at high temperatures and humidity. Surprisingly, this aluminum salt compound had eliminated the inhibition times while maintained other desired high performance characteristics, such as high M/#, high sensitivity and low shrinkage of the media.

Preferably, the aluminum salt compound has the following formula:

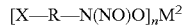

where, $X=H$, $CH_3$, $OCH_3$, F, Cl, $CF_3$ or $SOCH_3$; R is an aliphatic, alicyclic or aromatic group preferably having 1–18 carbon atoms; n=0–5; $M^2$ is hydrogen, a group I to III metal, a group VIIIB metal, or a substituted or unsubstituted NH4 group. Preferably $M^2$ is Al3+where n=3, and $M^2$ is $NH_4^+$ where n=0.

The most preferred compound is an aluminum salt, tri(N-nitroso-N-phenylhydroxylamine)aluminum salt (NPAL), available from Albemarle Corporation.

In particular, NPAL was found to be effective in preventing premature polymerization of the photoactive monomer. NPAL can be used by itself or in combination with other thermal stabilizers, for example, butyrated hydroxytoluene (BHT). The preferred amounts are from 0.001 to 0.1 wt. % of the total composition.

The invention will be further clarified by the following examples, which are intended to be exemplary.

Preparation of Novel Photoactive Compounds

I. 2,4-Bis(2-naphthylthio)-2-butylacylate

1. Preparation of 1,4-bis(2-naphthylthio)-2butanol, Compound 1

To a mixture containing potassium t-butoxide (2.69 g, 24 mmol) in acetone (40 ml) stirred at RT was added 2-naphthalenethiol (3.21 g, 20 mmol). A red color developed, the solids became dissolved and the mixture was stirred for another 15 min. 1,4-Dibromo-2-butanol (2.55 g, 11 mmol) was added over 15 min, and a precipitate was formed. After one hour, TLC (40% $CH_2Cl_2$/hexane) showed a complete disappearance of 2-naphthalenethiol. The mixture was filtered, washed with acetone (20 ml), and the filtrate was concentrated on rotovap. A brown solid obtained was crystallized from cyclohexane to yield Compound 1 as a yellow powdery solid (3.0 g, 76% yield). Recrystallization from iPrOH yielded pure Compound 1.

2. Preparation of 2,4-Bis(2-naphthalenethiol)-2-butylacrylate, Compound 2

To a solution containing the intermediate butanol Compound 1 (1.96 g, 5 mmol) and triethylamine (0.51 g, 5 mmol) in $CH_2Cl_2$ (40 ml) stirred at 0° C. was added acryloyl chloride (0.46 g, 5 mmol) and the solution was stirred for one hour. It was then washed with 5% $NaHCO_3$ (10 ml), deionized water (10 ml), dried over $MgSO_4$ and solvent removed on rotovap to yield Compound 2 as a yellowish, viscous oil (2.10 g, 94%).

II. 1,4-Bis(4-bromobenzenethiol)-2-butylacrylate

1. Preparation of 1,4-bis(4-bromophenylthio)-2-butanol, Compound 3

To a mixture of potassium t-butoxide (4.49 g, 40 mmol) in acetone (75 ml) stirred at RT was added 4-bromophenylthiol (7.56 g, 40 mmol) over a period of 15 min. Potassium t-butoxide became dissolved. To this mixture was added 1,4-dibromo-2-butanol (4.64 g, 20 mmol) and the mixture was stirred for one hour. The precipitate formed was filtered, wash with acetone (25 ml), and solvent removed on rotovap to give 1,4-bis(4-bromobenzenethiol)-2-butanol Compound 3 as a yellowish solid. Compound 3 was recrystallized twice from cyclohexane to yield white, fluffy crystals (4.67 g, 52%).

2. Preparation of 1,4-bis(4-broobezenethiol)-2-butylacrylate, Compound 4

To a solution of the intermediate butanol Compound 3 (4.48 g, 10 mmol) and triethylamine in THF (50 ml) and stirred at 0° C. was added acryloyl chloride (0.91 g, 10 mmol). A white precipitate appeared. The solution was stirred for one hour. It was filtered, washed with THF (20 ml). It was then washed with 5% NaHCO3 (15 ml), water (15 ml), dried (MgSO4), and concentrated over Rotovap to yield 4 as a near colorless oil in a quantitative yield.

EXAMPLES AND COMPARATIVE EXAMPLES

To fabricate the high temperature and humidity resistant recording article, the NCO-terminated prepolymer and polyol must first be reacted to form a matrix in which the acrylate monomer, which remains unreacted, will reside.

As the reaction of the NCO-terminated prepolymer and polyol are two-component system, the NCO-terminated prepolymer, acrylate monomer, photoinitiator, and thermal stabilizers are predissolved to form a homogeneous solution before charging into one of the holding tanks of a Posiratio two-component metering, mixing and dispensing machine, available from Liquid Control Corp. The polyol, tin catalyst, and other additives are premixed and charged into another holding tank. Each tank is then degassed, adjusting dispensing of materials from the tanks to the desired amount according to the procedures outlined by Liquid Control.

Precise and accurate mixing of the two components, free of entrapped air bubbles, is carried out by metering the liquid from both tanks simultaneously into a helical element static mixer.

To form a holographic recording article, the desired amount of the well-mixed solution is dispensed onto the inner surface of the bottom substrate held by one of the parallel plate. The upper substrate, which is held by the other parallel plate, is then brought down to come in contact with the solution and held at a predetermined distance from the bottom plate, according to the procedures described in U.S. Pat. No. 5,932,045 issued Aug. 3, 1999, the disclosure of which is hereby incorporated by reference. The entire set-up is held till the solution becomes solidified to assure an optically flat article is produced.

High performance holographic recording articles are characterized by low shrinkage, dynamic range, and sensitivity. Low shrinkage will assure non-degradation of the recorded holograms and total fidelity of the holographic data to be recovered. Low shrinkage in the range of less than 0.2% is required. The dynamic range of a holographic recording medium is typically characterized by the parameter, M/#, a measure of how many holograms of a give average diffraction efficiency can be stored in a common volume. The M/# is determined by both the refractive index contrast and thickness of a medium. Typical values of M/# are 1.5 or better. The photosensitivity is characterized by the total exposure time required to consume the dynamic range of the media. The sensitivity can be in the range of 5 to 600 seconds.

Details of the measurements of the recording-induced shrinkage, M/#/200 µm, and sensitivity are described in detail in Applied Physics Letters, Volume 73, Number 10, p. 1337–1339, 7 Sep. 1998, which is incorporated herein by reference. Angle-multiplexing a series of plane-wave holograms into the recording medium produce these measurements. A frequency-doubled diode-pumped Nd:YAG laser used for recording and recovery of the multiplexed holograms was spatially filtered and collimated by a lens to yield a plane-wave source of light. The light was then split into two beams by polarizing beam splitters and half-wave plates and intersected at the sample at an external angle of 44°. The power of each beam was 2 mW and the spot diameter was 4 mm. Each hologram is written with a predetermined exposure time. After recording, the material was allowed to sit in the dark for 20 minutes and then flood cured with a Xenon lamp filtered to transmit wavelengths longer than 530 nm.

COMPARATIVE EXAMPLE

This comparative example was prepared and evaluated in accordance with the procedures described above except using the following ingredients to illustrates the performance characteristics of a commercially available photoactive compound, tribromophenylacrylate.

| Component 1, Tank A | Baytech WE-180 | 415.7 gm |
|---|---|---|
| | Tribromophenylacrylate | 38.0 gm |
| | Irgacure 784 | 8.44 gm |
| | BHT | 210 mg |
| Component 2, Tank B | Polypropylene Oxide Triol | 577 gm |
| | t-Butylperoxide 310 | µl |
| | Dibutyltindilaurate | 10.2 gm |
| Properties o the articles | | |
| Shrinkage | 0.1% | |
| Dynamic range, M/#/200 µm | 2.40 | |
| Sensitivity, seconds to write 80% of the sample | 25 | |

1)Baytech WE-180, available from Bayer, is a 50/50 blend of biscyclohexylmethane diisocyanate and a NCO-terminated prepolymer based on biscyclohexylmethane diisocyanate and polytetramethylene glycol.
2)Polypropylene Oxide Triol of 1000 molecular weight.

EXAMPLE 1

Samples of Example 1 were prepared and evaluated in accordance with the procedures of Comparative Example except using the following ingredients to illustrates the performance characteristics of 2,4-bis(2-naphthylthio)-2-butylacrylate.

| Component 1, Tank A | Baytech WE-180 | 309.65 gm |
|---|---|---|
| | 2,4-Bis(2-naphthylthio)-2-butylacrylate | 42.11 gm |
| | Irgacure 784 | 8.05 gm |
| | BHT | 206 mg |
| Component 2, Tank B | Polypropylene Oxide Triol | 664 gm |
| | t-Butylperoxide | 310 µl |
| | Dibutyltindilaurate | 10.3 gm |
| Properties of the articles | | |
| Shrinkage | 0.07% | |
| Dynamic range, M/#/200 µm | 5.67 | |
| Sensitivity, seconds to write 80% of the sample | 41 | |

Polypropylene Oxide Triol of 1500 molecular weight.

EXAMPLE 2

Samples of Example 2 were prepared and evaluated in accordance with the procedures of Comparative Example except using the following ingredients to illustrates the performance characteristics of 1,4-bis(4-bromobenzenethio)-2-butylacrylate.

| | | |
|---|---|---|
| Component 1, Tank A | Baytech WE-180 | 309.65 gm |
| | 1,4-Bis(4-bromobenzenethio)-2-butylacrylate | 47.87 gm |
| | Irgacure 784 | 8.03 gm |
| | BHT | 206 mg |
| Component 2, Tank B | Polypropylene Oxide Triol | 664 gm |
| | t-Butylperoxide | 310 μl |
| | Dibutyltindilaurate | 12.5 gm |
| Properties of the articles | | |
| Shrinkage | 0.06% | |
| Dynamic range, M/#/200 μm | 4.07 | |
| Sensitivity, seconds to write 80% of the sample | 22 | |

Polypropylene Oxide Triol of 1500 molecular weight.

The above description is presented to enable a person skilled in the art to make and use the invention, and is provided in the context of a particular application and its requirements. Various modifications to the preferred embodiments will be readily apparent to those skilled in the art, and the generic principles defined herein may be applied to other embodiments and applications without departing from the spirit and scope of the invention. Thus, this invention is not intended to be limited to the embodiments shown, but is to be accorded the widest scope consistent with the principles and features disclosed herein. This application discloses several numerical range limitations. The numerical ranges disclosed inherently support any range within the disclosed numerical ranges even though a precise range limitation is not stated verbatim in the specification because this invention can be practiced throughout the disclosed numerical ranges. The entire disclosure of the patents and publications referred in this application are hereby incorporated herein by reference.

What is claimed is:

1. A photosensitive composition comprising a photoinitiator and a photoactive compound comprising a chemical structure represented by

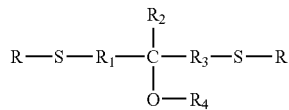

wherein R is a bromophenyl group or a naphthalene group; $R_1$ and $R_3$ are a methylene group, an ethylene group, a propylene group, or a butylene group; $R_2$ is H or an alkyl group; and $R_4$ is $COCH=CH_2$, $COC(CH_3)=CH_2$, or $CH=CH_2$ and the photoactive compound is a monomer for a photoimageable system.

2. The photosensitive composition of claim 1, wherein said photoactive monomer forms a polymer.

3. The photosensitive composition of claim 1, wherein the photoimageable system forms a holographic recording medium having a dynamic range of greater than 3 and a shrinkage of less than 0.1%.

4. The photosensitive composition of claim 3, wherein the shrinkage is less than 0.08%.

5. The photosensitive composition of claim 4, wherein the dynamic range is greater than 4.

6. A photoimageable system comprising a matrix precursor, a photoinitiator and a photoactive compound comprising a chemical structure represented by

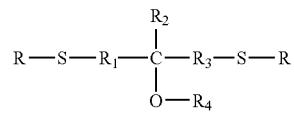

wherein R is a bromophenyl group or a naphthalene group; $R_1$ and $R_3$ are a methylene group, an ethylene group, a propylene group, or a butylene group; $R_2$ is H or an alkyl group; and $R_4$ is $COCH=CH_2$, $COC(CH_3)=CH_2$, or $CH=CH_2$.

7. The photoimageable system of claim 6, wherein the photoimageable system is a two-chemistry system.

8. The photoimageable system of claim 7, wherein the matrix precursor forms a urethane.

9. The photoimageable system of claim 6, wherein the photoimageable system forms a holographic recording medium having a dynamic range of greater than 3 and a shrinkage of less than 0.1%.

10. The photoimageable system of claim 9, wherein the photoimageable system forms a holographic recording medium having a dynamic range of greater than 4 and a shrinkage of less than 0.08%.

* * * * *